(12) United States Patent
Naser et al.

(10) Patent No.: US 7,863,040 B2
(45) Date of Patent: Jan. 4, 2011

(54) READY-TO-USE WHOLE BLOOD COLLECTION VESSEL

(75) Inventors: Werner Naser, Penzberg (DE); Thomas Duelffer, Weilheim (DE); Rupert Herrmann, Weilheim (DE); Uwe Kobold, Weilheim (DE); Herbert von der Eltz, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 117 days.

(21) Appl. No.: 12/327,854

(22) Filed: Dec. 4, 2008

(65) Prior Publication Data

US 2009/0246866 A1  Oct. 1, 2009

Related U.S. Application Data

(63) Continuation of application No. PCT/EP2007/004925, filed on Jun. 4, 2007.

(30) Foreign Application Priority Data

Jun. 6, 2006  (EP) .................................. 06011606

(51) Int. Cl.
  C12M 1/33 (2006.01)
  C12M 3/08 (2006.01)
(52) U.S. Cl. ................................................. 435/306.1
(58) Field of Classification Search .................... 435/4, 435/7, 7.92, 14, 29, 18, 306.1; 436/8, 17.63; 252/408.1; 600/573, 576, 577; 250/282
See application file for complete search history.

(56) References Cited

U.S. PATENT DOCUMENTS

| | | | | |
|---|---|---|---|---|
| 4,297,238 A | * | 10/1981 | Vormbrock et al. | 436/17 |
| 4,656,139 A | * | 4/1987 | Matsuda et al. | 436/17 |
| 5,116,615 A | | 5/1992 | Gokcen et al. | |
| 5,180,677 A | * | 1/1993 | Di Ianni et al. | 436/17 |
| 5,874,310 A | * | 2/1999 | Li et al. | 436/10 |
| 6,050,956 A | | 4/2000 | Ikegami et al. | |
| 6,322,695 B1 | | 11/2001 | Lee et al. | |
| 6,723,236 B2 | | 4/2004 | Fisk et al. | |

FOREIGN PATENT DOCUMENTS

| | | |
|---|---|---|
| EP | 0185048 B1 | 6/1986 |
| EP | 0305491 B1 | 2/1996 |
| EP | 0874988 B1 | 11/1998 |
| EP | 0743519 B1 | 8/2002 |
| EP | 1000356 B1 | 11/2004 |
| EP | 1637883 A1 | 3/2006 |
| JP | 59196084 A | 11/1984 |

OTHER PUBLICATIONS

Bunting, P. et al., :Interference from Renal Dialysis Patients' Specimens in a Direct Method for Serum Iron, Clin. Chem. 29:6 (1983) 1106-1108.
Carrera Font, T. et al., "Evaluacion de un procedimiento de medida de hemoglobin A1c en una gota de sangre recogida sobre papel de filtro," Quimica Clinical 20:2 (2001) 53-56.
Fazili, Z. et al., "Erythrocyte Folate Extraction and Quantitative Determination by Liquid Chromatography-Tandem Mass Spectrometrhy: Comparison of Results with Microbiologic Assay," Clinical Chemistry 51:12 (2005) 2318-2325.
Gunter, E. et al., "Results of an international round robin for serum and whole-blood folate," Clinical Chemisty 42:10 (1996) 1689-1694.
Jaynes, P. et al., "Evaluation of a Mini-Column Chromatographic Procedure for the Measurement of Hemoglobin A1c," Clinical Biochemistry 18 (Feb. 1985) 32-36.
Jones, K. et al., "An Immunoassay for the Measurement of Sirolimus," Clinical Therapeutics 22: Suppl B (2000) B19-B61.
Karl, J. et al., "Development and Standardization of a New Immunoturbidimetric HbA1c Assay," Klin. Lab 39 (1993) 991-996.
Murthy, J. et. al., "Tacrolimus Metabolite Cross-Reactivity in Different Tacrolimus Assays," Clinical Biochemistry 31:8 (1998) 613-617.
Pfeiffer, C. et al., "Determination of Folate Vitamers in Human Serum by Stable-Isotope-Dilution Tandem Mass Spectrometry and Comparison with Radioassay and Microbiologic Assay," Clinical Chemistry 50:2 (2004) 423-432.
"Therapeutic drug monitoring—is it important for newer immunosuppressive agents?" Drug Ther Perspect 17 (2001) 8-12.

\* cited by examiner

Primary Examiner—Walter D Griffin
Assistant Examiner—Shanta G Doe
(74) Attorney, Agent, or Firm—Marilyn L. Amick; Roche Diagnostics Operations, Inc.

(57) ABSTRACT

The present invention relates to a sampling tube for collecting and processing a whole blood sample. The sampling tube contains a reagent for differential hemolysis of whole blood, wherein said reagent for differential hemolysis comprises a chemical for differential hemolysis and an anti-coagulant, and wherein said sampling tube is a ready-to-use and single-use sampling tube. It also relates to the use of said sampling tube in the processing of a whole blood sample for liquid chromatography and also to the use of a blood sample processed in such sampling tube in a liquid chromatography-based analysis.

3 Claims, 4 Drawing Sheets

READY-TO-USE WHOLE BLOOD COLLECTION VESSEL

RELATED APPLICATIONS

This application is a continuation of PCT/EP2007/004925 filed Jun. 4, 2007 and claims priority to EP 06011606.8 filed Jun. 6, 2006.

FIELD OF THE INVENTION

The present invention relates to a sampling tube for collecting and processing a whole blood sample. The sampling tube contains a reagent for differential hemolysis of whole blood, wherein said reagent for differential hemolysis comprises a chemical for differential hemolysis and an anti-coagulant, and wherein said sampling tube is a ready-to-use and single-use sampling tube. It also relates to the use of said sampling tube in the processing of a whole blood sample for liquid chromatography and also to the use of a blood sample processed in such sampling tube in a liquid chromatography-based analysis.

BACKGROUND OF THE INVENTION

In clinical routine blood is the most important source of sample to be analyzed. Though whole blood is the first sample obtained, the whole blood sample usually has to be further processed in order to allow for convenient sample handling or for reliable analyte detection.

The more constituents are present in a sample the more difficult is the analysis of a target analyte comprised therein. Red blood cells contain a dramatic amount of proteins and small molecular weight constituents that potentially interfere with any analyte to be detected. This is one of the major reasons why in clinical routine preferably blood plasma (often simply referred to as plasma, i.e., an anticoagulated whole blood sample; deprived of cells and erythrocytes) or blood serum (often simply referred to as serum, i.e., coagulated whole blood; deprived of cells, erythrocytes and most proteins of the coagulation system, especially of fibrin/fibrinogen), respectively, are used. Whole blood samples also tend to be more difficult to handle, e.g., as compared to serum or plasma. Whole blood tends to be less stable and slow rupture of erythrocytes impairs a reliable measurement of quite a few analytes of interest. In addition, transport and storage of a whole blood sample requires special measures of precaution.

In case an analyte has to be measured from whole blood, it is general practice to collect the whole blood sample and to treat such sample during or immediately after collection of blood with an appropriate anti-coagulant. In clinical routine tubes prefilled with an appropriate anti-coagulant are used for collection of whole blood samples. As the name tells these anti-coagulants block the activation of the coagulation system. Blood cells and erythrocytes shall remain intact as much and as long as possible. The anti-coagulated blood has to be handled very carefully in order to avoid problems, e.g., caused by sedimentation of blood cells or erythrocytes or caused by lysis of erythrocytes. Usually aliquots of such anti-coagulated whole blood sample are then used in the detection of an analyte of interest, e.g., of an analyte that is at least partially comprised within red blood cells.

In addition, at this point in time it does not appear to be feasible to use a whole blood sample in any of the existing online detection methods. It is for example not possible to use a whole blood sample in a clinical diagnostic routine procedure requiring a separation step based on liquid chromatography (LC). Routine liquid chromatographic separation usually is based on a column essentially consisting of a filter unit or frit to protect the column material and the column material required for the separation of the analyte(s) of interest. If whole blood is applied to such column, the column will be blocked rather soon or even immediately, depending on column size and system. This problem makes it merely impossible to use whole blood in an online detection process in combination with an LC-method as for example preferred in clinical routine diagnosis. At present it appears that appropriate separation/handling of a blood sample, e.g., by centrifugation, filtration, precipitation or analyte extraction is essential, before such processed sample can be properly and reliably analyzed.

As indicated above, serum or plasma may be obtained from whole blood and used in the detection of an analyte. Cells and erythrocytes in theory may also be removed by filtration or centrifugation from whole blood. However, these methods are neither appropriate for use in a routine diagnostic setting, nor would they allow for a correct measurement of those analytes at least partially present inside red blood cells.

In a further way of sample processing the analyte of interest is first separated from the majority of potentially interfering substances by selective precipitation or extraction methods. Extraction can be performed in liquid phase or on a solid phase. This shall be exemplified by illustrating some of the procedures used in the detection of immunosuppressive drugs.

Well-known immunosuppressive drugs are, e.g., mycophenolate mofetil (MMF), rapamycin (RAPA also known as sirolimus) and tacrolimus (FK-506). Therapeutic drug monitoring for immunosuppressive drugs is especially important for transplant patients as well as for patients suffering from AIDS (cf., e.g.: Drug. Ther. Perspect 17 (2001) 8-12). Most patients who undergo solid organ transplantation require lifelong immunosuppressive therapy to prevent allograft rejection. But, because many immunosuppressive agents have narrow therapeutic ranges also referred to as therapeutic window, and are associated with various toxicities and the potential for drug interactions, the use of therapeutic drug monitoring (TDM) in conjunction with clinical assessment of patients may be particularly important.

Mycophenolate mofetil is a prodrug. After oral administration, mycophenolate mofetil (MMF) undergoes rapid hydrolysis in the intestine and blood to form its active metabolite mycophenolic acid (MPA). MMF is widely available and is approved in the US and UK for the prevention of renal, hepatic or cardiac allograft rejection in combination with corticosteroids and cyclosporin. The drug has demonstrated superiority over azathioprine in reducing the incidence of acute rejection of renal allografts. The therapeutic trough concentration is in the range of 1-3.5 mg/L. MMF can be measured from plasma and from whole blood.

Tacrolimus is a macrolide antibiotic that was first approved by the US Food and Drug Administration (FDA) in 1994 for the prevention of liver allograft rejection. It is up to 100 times more potent than cyclosporin in vitro, and clinically, it is associated with a greater reduction in the incidence of tissue rejection. Tacrolimus has demonstrated efficacy both as primary immunosuppressive therapy in patients undergoing various transplantation procedures and as rescue therapy for patients with refractory acute allograft rejection after liver or kidney transplantation. The therapeutic trough concentration is in the range of 5-20 µg/L.

Since at least part of the tacrolimus present in the circulation is compartmented within erythrocytes, a whole blood sample is used in the clinical routine measurement of this drug. Tacrolimus can, e.g., be detected by high performance liquid chromatography (HPLC), HPLC mass spectrometry (MS), radio receptor assay (RRA), or by an immunoassay (IA). The latter two methodologies do not detect tacrolimus and certain of its various metabolites with the same sensitivity. This may lead to an interference in the procedure used (Murthy, J. N., et al., Clin. Biochem. 31 (1998) 613-617). At least in the detection of the various tacrolimus metabolites the HPLC-MS-procedure may be considered the gold standard. All the procedures mentioned above, however, require the extraction of tacrolimus from whole blood. Usually acetonitrile is used in clinical routine for the extraction of tacrolimus from whole blood and no method appears to exist that would allow for an online measurement of tacrolimus from a whole blood sample.

Sirolimus is, like tacrolimus, a macrolide antibiotic. It was first approved in 1999 by the US FDA for the prevention of allograft rejection after kidney transplantation, and indeed has shown promising results in this respect when used acutely in combination with cyclosporin and corticosteroids. In vitro, sirolimus is up to 100 times more potent than cyclosporin, and clinically, it may exhibit synergism with cyclosporin, perhaps permitting a reduction in cyclosporin dosage. The therapeutic trough concentration is in the range of 5-15 μg/L.

As for tacrolimus, a significant amount of sirolimus is present within erythrocytes. Therefore extraction of a whole blood sample is required no matter which detection method is used. In clinical routine a sample suspected to comprise sirolimus is subjected to HPLC and sirolimus is detected by ultraviolet light (UV) or by MS/MS. Recently also a microparticle enzyme immunoassay has been described (Jones, K., et al., Clinical Therapeutics 22, Suppl. B (2000) B49-B61).

Folate is the collective name of a group of related molecules differing in oxidation state. Folates are part of the water-soluble vitamin B group and are important as coenzymes for homocysteine metabolism and in the transfer of one-carbon groups required for DNA replication. Inadequate folate status is related to increased risk of neural tube defects, is associated with cardiovascular disease, anemia, with certain cancers and with Alzheimer's disease. Serum or plasma folate concentrations reflect recent dietary intake, whereas erythrocyte folate concentrations are more indicative of body stores (Gunter, E. W., et al., Clin. Chem. 42 (1996) 1689-1694; Fazili, Z., et al., Clin. Chem. 51 (2005) 2318-2325; Pfeiffer, C. M., et al., Clin. Chem. 50 (2004) 423-432). Erythrocyte total folate (red blood cell folate=RBC-folate) is the best measure of whole body folate status. Recent studies have shown that 5-methyl tetrahydrofolate is the dominant folate vitamer in circulating erythrocytes. For the diagnosis of folate deficiency it is recommended that determinations are performed not only from serum or from plasma but also from erythrocytes, since folate is localized to more than 95% in the latter. The concentration in the erythrocytes more truly reflects the actual folate status.

A number of methods are available to measure folate in different matrices. The major analytical methods are microbiological assay, radio immuno assay, chemiluminescence, chromatographic methods and mass spectrometric methods. Most methods are based on competitive binding of folate to folate binding protein.

For the measurement of RBC-folate the use of a hemolyzing reagent is obviously mandatory. For example the ELECSYS assay (Roche Diagnostics GmbH) for determination of RBC folate uses ascorbic acid as lysis reagent. ELECSYS RBC-folate hemolyzing reagent is used together with the ELECSYS folate assay for the quantitative determination of folate in erythrocytes (RBC-folate). Whole blood treated with anticoagulants (heparin or EDTA) is diluted with ascorbic acid solution (0.2%) and incubated for approximately 90 minutes at 20-25° C. Lysis of the erythrocytes takes place, with liberation of the intracellular folate. The hemolysate is then used as a "prediluted" sample (in analogy to serum) for subsequent measurement in the ELECSYS folate assay. The hematocrit value determined in whole blood and the dilution effect brought about by pretreatment of the sample is compensated for in the calculation of the erythrocyte folate concentration (Greiling, H., Gressner, A. M., Lehrbuch der Klinischen Chemie und Pathobiochemie, 3rd ed., Stuttgart, N.Y., Schattauer (1995) pp. 460-462; Gunter, E. W., et al., Clin. Chem. 42 (1996) 1689-1694).

The hemolysate generated by treatment with ascorbic acid can not be used for routine chromatographic procedures. For use of such hemolysate in chromatographic procedure or mass spectrometric determination it is necessary to remove cell debris and precipitated protein prior to analysis.

Debris and precipitated proteins usually are removed from a sample by centrifugation, offline filtration or solid phase extraction.

Solid phase extraction (SPE) is a chromatographic technique which is widely used, e.g., for preconcentration and cleanup of analytical samples, for purification of various chemicals, and for removal of toxic or valuable substances from aqueous solutions. SPE is usually performed using a column or cartridge containing an appropriate resin. SPE procedures have been developed using sorbents which can interact with analytes by hydrophobic, ion exchange, chelation, sorption, and other mechanisms, to bind and remove the analytes from fluids. Since different SPE applications for different classes of analytes can require different sorbents, there is a concomitant need for sorbents with specific properties which have unique selectivity for the analyte or class of analytes of interest, Representative examples of SPE materials and SPE columns, respectively, can be found in U.S. Pat. No. 6,322,695 and U.S. Pat. No. 6,723,236.

Alike to quite a few other analytes of interest, there appears to be no method available that would allow for the detection of sirolimus or tacrolimus in an online procedure from a whole blood sample.

The concentration of hemoglobin itself as well as the ratio of glycated hemoglobin (HbA1c) to non-glycated hemoglobin are important analytes in hematology and diabetes. In such assessment the erythrocytes comprised in a whole blood sample are lysed and the hemoglobin is then measured. U.S. Pat. No. 6,050,956 describes a hemolyzing tube that is prefilled with a standardized amount of a blood dissolving liquid. However, whole blood is first collected into a routine blood collection tube. Thereafter blood is diluted 1 plus 100 into the hemolyzing tube. Due to the very high concentration of hemoglobin a 1 plus 100 dilution of whole blood is possible and no differential hemolysis, i.e., no hemolysis avoiding negative side effects like protein precipitation and/or release of DNA, is required Various patent families to Coulter International Inc., like U.S. Pat. No. 5,874,310; EP 1 000 356; EP 0 874 988; EP 0 305 491 or EP 0 185 048 relate to the field of hematology and especially to the analysis of blood cells. EP 1 000 356, e.g., describes an improved diluent for dilution of a blood sample that is suited for enumeration and sizing of blood cells, determination of hemoglobin parameters and differentiation of leukocyte sub-populations in a single blood sample. Analysis is performed by use of suitable electronic instrumentation. For such analysis blood is usually collected by a physician, then has to be transported to the clinical laboratory, and only shortly before analysis a lysis reagent is added.

Obviously careful transport of an anti-coagulated whole blood sample is crucial. Freezing and elevated temperature must be avoided. There also is a significant biohazard associated to the transport of an anti-coagulated whole blood sample. A tube that leaks or breaks during transport may contaminate packaging material or might be infectious.

It becomes obvious from the above discussion of the state of the art that whole blood still is a stepchild in clinical routine. All routine procedures even today appear to require an anti-coagulation treatment, high dilution of the sample, and/or the separation or fractionation of an analyte of interest or of a certain class of compounds from the rest of compounds comprised in such sample. In addition, no method for an online measurement of a whole blood sample appears to be available.

It would, however, be highly desirable if whole blood could be used directly and easily as a sample. This would be especially advantageous in an online detection procedure making use of a liquid chromatographic (LC) separation step. It is also obvious that the direct processing of a whole blood sample rendering the processed sample more easy to store, handle and transport would represent an important progress for clinical routine diagnostic applications.

It has now surprisingly been found and could be established that it is possible with great advantages to collect a sample of whole blood into a ready-to-use and single use whole blood sampling tube that is prefilled with a reagent for differential hemolysis of said whole blood sample. The sampling tube according to the present invention greatly facilitates the use of a whole blood sample, renders the handling of such sample and also the transport of such sample easy and convenient, and allows for the direct detection of analytes from a whole blood sample. The collection of whole blood in a sampling tube according to the present invention, e.g., renders whole blood an appropriate sample for direct separation by chromatography and analyte detection, e.g., by mass spectroscopy. This is especially valuable for an analyte that is also present to a relevant extend inside red blood cells, like folate or the immunosuppressive drugs sirolimus and tacrolimus.

SUMMARY OF THE INVENTION

In a first embodiment the present invention relates to a sampling tube for collecting and processing a whole blood sample, the sampling tube containing a reagent for differential hemolysis of said whole blood sample, wherein said reagent for differential hemolysis comprises a chemical for differential hemolysis and an anti-coagulant, and wherein said sampling tube is a ready-to-use and single-use sampling tube.

In a further embodiment the present invention relates to the use of the sampling tube according to present invention in the processing of a whole blood sample for liquid chromatography.

In a further embodiment the present invention describes the use of a processed blood sample obtained by differential hemolysis within a sampling tube according to this invention in a liquid chromatography-based analysis.

The present invention also relates to the use of a reagent composition appropriate for differential hemolysis of a whole blood sample in the processing of a whole blood sample for liquid chromatography, wherein said reagent composition comprises an anti-coagulant.

DETAILED DESCRIPTION OF THE INVENTION

Figure 1:
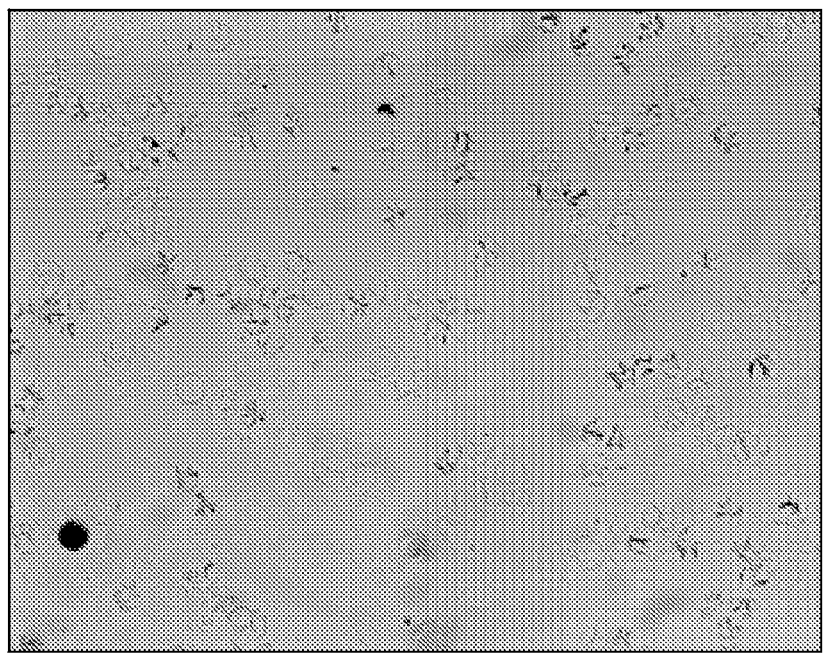
FIG. 1: Light microscopy of a 1 in 10 diluted whole blood hemolyzed with water. May-Grünwald staining has been applied. Erythrocyte membranes and nuclei are visible.

In a preferred embodiment the present invention relates to a sampling tube for collecting and processing a whole blood sample, the sampling tube containing a reagent for differential hemolysis of said whole blood sample, wherein said reagent for differential hemolysis comprises a chemical for differential hemolysis and an anti-coagulant, and wherein said sampling tube is a ready-to-use and single-use sampling tube.

An "anticoagulant" in the sense of the present invention is an agent used to keep a laboratory blood specimen from clotting. These agents include heparin and several agents that make calcium ions unavailable to the clotting process and so prevent the formation of clots; these agents include for example ethylenediaminotetraacetic acid (commonly called EDTA), EGTA, citrate, oxalate and fluoride. Preferred anticoagulants for use in a reagent for differential hemolysis in a sampling tube according to the present invention are heparin, EGTA and citrate. Preferably the anticoagulant is heparin or citrate.

A "sampling tube" according to the present invention may be any device with a reservoir appropriate for receiving the blood sample to be collected. As the skilled artisan will appreciate the sampling tube preferably will in fact be a tube. Preferably the sampling tube has a size and dimension adapted to match the requirements of the sample receiving station of an automated analyzer, e.g., an ELECSYS analyzer of Roche Diagnostics. The sampling tube may have a conical or preferably a round bottom. In clinical routine standard tube sizes are used that are compatible with the analyzers systems on the market. Standard and preferred tubes, e.g., have the following dimensions: 13×75 mm; 13×100 mm, or 16×100 mm.

The articles "a" and "an" are used herein to refer to one or to more than one (i.e., to at least one) of the grammatical object of the article. By way of example, "a red blood cell" means one red blood cell or more than one red blood cell.

The sampling tube according to the present invention is prefilled with a reagent for differential hemolysis, i.e., it is containing this reagent. The tube is provided to the customer in a ready-to-use form. The customer does not need to prepare or handle the reagent for differential hemolysis, since this is provided in an amount and concentration appropriate to achieve the differential hemolysis of the blood sample.

In a further preferred embodiment the sampling tube of the present invention has an inner pressure below the atmospheric pressure. Preferably the sampling tube accommodates the advantages associated with the Vacutainer® brand line as distributed by BD Diagnostics, Franklin Lakes, N.J.

The blood collection tube according to the present invention is only used once, i.e., it is a single-use device.

The sampling tube according to the present invention is not only appropriate for collection of a whole blood sample but it also adapted to allow for the processing of the whole blood sample. By collecting a whole blood into a prefilled sampling tube containing the reagent for differential hemolysis, the desired result, i.e., differential hemolysis is achieved.

In a further preferred embodiment of the present invention the sampling tube for collecting and processing a whole blood sample is further characterized in that the reagent for differential hemolysis is causing the lysis of cell membranes of red blood cells and at the same time is not causing precipitation of sample constituents.

"Red blood cells" in the sense of the present invention are red blood cells not having a cell nucleus. Such red blood cells not having a cell nucleus are, e.g., the mature red blood cells as found in the circulation of mammals. This invention does not relate to nucleated red blood cells as, e.g., known from avian species. The later ones would meet the criteria for nucleated or eukaryotic cell.

"Mammal" for purpose of the present invention refers to any animal classified as a mammal, including humans, domestic and farm animals, and zoo, sports, or pet animals, such as dogs, cats, cattle, horses, sheep, pigs, goats, rabbits, etc. Preferably, the mammal is human.

A "eukaryotic cell" or a "nucleated cell" in the sense of the present invention is a cell derived from a eukaryotic organism and is still having its cell nucleus. Examples of eukaryotic cells are cells derived from nucleated tissue, nucleated tissue culture cells and nucleated blood cells. In a preferred embodiment the eukaryotic cell is a nucleated blood cell like a thrombocyte, a monocyte, neutrophils, eosinophils or a leukocyte. Cells from lower organisms, like bacteria, though containing genetic material, are not eukaryotic cells.

According to the present invention a whole blood sample is filled into the ready-to-use-sampling tube. The sample is mixed with the reagent for differential hemolysis comprised in said tube, thereby differential hemolysis is achieved. Use of the appropriate reagent for differential hemolysis ensures that two requirements are met: a) the membranes of red blood cells are lysed and b) and at the same time no precipitation of sample constituents is caused. This process: i.e., disrupting the membranes of red blood cells but at the same time not causing precipitation of sample constituents, is termed here differential hemolysis. The processed sample is referred to as differentially hemolyzed blood or as differentially hemolyzed blood sample.

Preferably the reagent for differential hemolysis will bring about the lysis of at least 95% of the erythrocytes present in a sample. Further preferred the reagent for differential hemolysis will bring about the lysis of at least 97%, 98%, 99%, 99.5% of the erythrocytes present in a sample.

Without wanting to be bound to the following theory one may assume that the advantageous balance at which the membrane of a red blood cell is disrupted but at which at the same time no precipitation of sample constituents is caused is essential for overcoming at least some of the problems known from the art. By applying an appropriate reagent for differential hemolysis under appropriate conditions the integrity of the cellular membrane that is, e.g., essential for shielding the contents of a red blood cell from the blood plasma is lost. The content of the erythrocytes (e.g. hemoglobin but also some analytes of interest) is released into the surrounding liquid. At the same no precipitation of sample constituents is caused.

As the skilled artisan will appreciate, sample constituents that might interfere with a latter analysis may especially be DNA and de-natured proteins, respectively. As long as the nuclei of eukaryotic cells, e.g., like lymphocytes or monocytes are not destroyed, no DNA is released from these nuclei. As long as no proteins precipitate, proteins comprised in the sample subjected to differential hemolysis will not interfere, at least not to a significant extend, with the chromatography step or with the analysis.

The integrity of red blood cells can for example be easily assessed by appropriate life stains. In a preferred embodiment according to the present invention trypane blue is used in order to assess the integrity of a red blood cell membrane. Intact red blood cells do not accumulate trypane blue, whereas a red blood cell with a disrupted membrane does stain with trypane blue. The membrane integrity of a red blood cell is easily assessed under the microscope after staining a sample with trypane blue. The percentage of disrupted red blood cells is calculated by counting intact red blood cells before and after the treatment, by then dividing the first number by the latter number and by then multiplying this value by 100. Red blood cells that are solubilized are referred to as lyzed red blood cells or as lyzed erythrocytes.

The appropriate treatment will be suitable to lyse a red blood cell, but at the same time it will not cause precipitation of sample constituents. It is expected that the appropriate hemolysis treatment in a method according to the present invention will also effects the outer membranes of eukaryotic cells. However, care can and must be taken that the DNA contained in the cell nuclei is not released into the sample. The hemolysis reagent and the conditions for differential hemolysis used will either and preferably leave the nuclear membrane and thus the nuclei macroscopically intact or at least DNA will not be set free from its surrounding and DNA-stabilizing nuclear proteins. If DNA would be released to a significant extend such DNA might or even would interfere with further handling of the sample. Released DNA, e.g., tends to make the liquid very viscous. It is then no longer possible to pipette or transfer such sample or to pass it through certain filters or columns.

Care can and must also be taken that no protein precipitation occurs. As the skilled artisan will appreciate, there are many, many different proteins present in a biological sample, e.g., in a whole blood sample. All these proteins have individual properties influencing their tendency to precipitate or aggregate.

It has now been found that it is possible to describe and define whether sample processing with the reagent for differential hemolysis is—as the term indicates—performed under appropriate conditions in order lyse cell membranes of red blood cells on the one hand and at the same time not to cause precipitation of sample constituents. Both, red blood cells not lysed as well as precipitated sample constituents have a negative impact on the properties of such sample.

Whether the conditions for differential hemolysis are appropriate can be easily and preferably determined by using the following standardized procedure. A whole blood sample with a hematocrit of 40 is diluted 1:10 and then mixed 1:1 with the candidate hemolysis reagent. The efficacy of a reagent for bringing about differential hemolysis is seen visually. Upon lysis of the erythrocytes the mixture becomes clear. If precipitation of sample constituents occurs the sample becomes turbid or viscous or both.

As indicated above, the conditions used in a method of differential hemolysis according to the present invention can easily be assessed visually. If a whole blood sample is incubated with an appropriate candidate reagent for differential hemolysis the minimal concentration required to hemolyze red blood cells can be recognized as the concentration rendering the turbid blood sample transparent or clear. The highest possible concentration is the one still leading to a transparent and non-viscous sample.

It has turned out rather easy to determine the appropriate minimal concentration of the candidate hemolysis reagent as the concentration leading to the change in transparency of a treated whole blood sample. This change in transparency correlates well with the suitability of such processed sample for direct analysis by HPLC.

The maximal concentration of hemolysis reagent possible is the concentration still not causing release of DNA and/or precipitation of a protein. The sample thereby would turn viscous or turbid or both and is not suitable for a direct HPLC application anymore. Whereas viscosity and turbidity can be followed visually it is preferred that maximal concentration of a hemolysis reagent is confirmed by an HPLC method as described below.

Both, a whole blood sample still comprising too many non-lysed erythrocytes as well as a treated whole blood sample comprising precipitated sample constituents will not be suitable for any chromatographic procedure. This is why the conditions appropriate to bring about differential hemolysis preferably are determined by applying in a standardized manner a sample of whole blood treated with a candidate reagent for differential hemolysis to an HPLC column.

Incomplete hemolysis and/or precipitation of sample constituents are assessed by applying 50 times 10 µl of the processed whole blood sample to an HPLC column. To assess whether a candidate chemical or reagent for differential hemolysis is appropriate, said hemolysis reagent is mixed with a sample of whole blood. Preferably EDTA-blood that has been prediluted 1:10 in physiological saline is used. It is mixed in a 1:1 ratio with the candidate hemolysis reagent and the mixture is incubated for 30 min at 20° C. The final dilution of whole blood in this mixture thus is 1:20. 50 aliquots of 10 µL of the this mixture, i.e., a processed whole blood sample are applied to a filter with a diameter of 2 mm and 0.5 µm pore size that is part of an HPLC system. In case the frit is part of an HPLC column the stationary phase must be selected not to cause any interference or blocking. The back-pressure is monitored. A candidate reagent for differential hemolysis that would cause an increase in back-pressure of 20 bar or more—if the back-pressure for injection 50 and the back-pressure for the first injection are compared to each other—would be deemed not to be appropriate. This way both the minimal as well as the maximal concentration of an appropriate reagent for differential hemolysis can easily be identified. The minimal concentration is the lowest concentration of the candidate hemolysis reagent leading to differential hemolysis as assessed in the above described setting.

Preferably the filter used in the above assessment of a candidate reagent for differential hemolysis is an HPLC frit. Also preferred the frit is part of an HPLC column of 20 mm in length filled with 3.5 µm Symmetry® C18 particles with a pore size of 100 Å as bed material, and having an inner column diameter of 2 mm.

As the skilled artisan will readily appreciate the whole blood sample used for such assessment is obtained from a healthy individual, i.e., an individual having no known disease and biochemical values in the normal range.

It has been found and established in the present invention that appropriate conditions can be established for quite many reagents in order to meet both the requirements for differential hemolysis.

The reagent for differential hemolysis according to the present invention preferably is based on water as a solvent, a chemical or reagent bringing about the differential hemolysis as described above, an anti-coagulant and also preferred may comprise a buffer, an enzyme and/or a preservative. A chemical for differential hemolysis is a membrane-solubilizing or membanenolytically active chemical. The reagent for differential hemolysis preferably is based on a hematolytically or membranolytically active chemical that has a molecular weight of less than 1000 Dalton and brings about differential membrane solubilization.

The reagent used for differential hemolysis preferably is based on one or more of the following hematolytically active chemicals: KBr; KJ; and KSCN or on a salt consisting of one or more of the following cations and anions:

The cation preferably is selected from

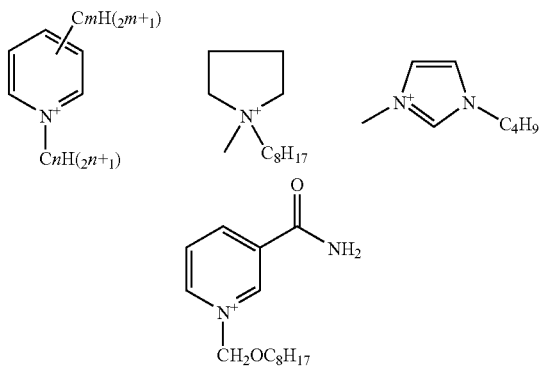

wherein m is 0 or 1 and n is 4 or 6.

The anion is preferably selected from chloride, tetrafluoroborate, octylsulfate, iodide and thiocyanate. It is also possible to use mixtures of the above mentioned chemicals. As the skilled artisan appreciates, it is these chemicals that facilitate the differential hemolysis whereas other ingredients of a hemolysis reagent may function as buffer or as preservative.

Preferably the chemical used for differential hemolysis is a salt wherein the cation preferably is selected from

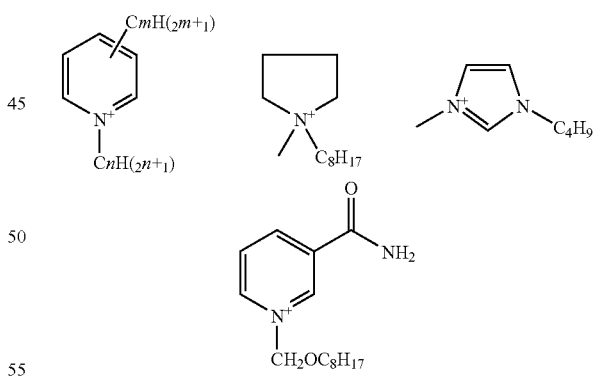

wherein m is 0 or 1 and n is 4 or 6, and wherein the anion is preferably selected from chloride, tetrafluoroborate, octylsulfate, iodide and thiocyanate.

Appropriate chemicals for differential hemolysis are preferably selected from the group consisting of 1-Butyl-4-methylpyridinium tetrafluoroborate; 1-Butyl-3-methyl-imidazolium tetrafluoroborate; 1-Butyl-3-methyl-imidazoliumoctylsulfate; 1-Butyl-3-methylpyridiniumchloride; 1-Hexylpyridiniumchloride; 1-Methyl-1-octyl pyrrolidiniumchloride; N-Octylpyridiniumchloride; 3-Carbamoyl-1-octyloxymethyl pyridiniumchloride; KBr; KJ; and KSCN, and of combinations thereof.

Also preferred the chemical used for differential hemolysis is selected from the group consisting of 1-Butyl-4-methylpyridiniumtetrafluoroborate; 1-Butyl-3-methyl-imidazoliumtetrafluoroborate; 1-Butyl-3-methyl-imidazoliumoctylsulfate; 1-Butyl-3-methylpyridiniumchloride; 1-Hexylpyridiniumchloride; 1-Methyl-1-octyl pyrrolidiniumchloride; N-Octylpyridiniumchloride; and 3-Carbamoyl-1-octyloxymethyl pyridiniumchloride. It is further preferred to use a mixture of one these reagents and of KSCN.

As obvious to the skilled artisan, once an appropriate concentration of a candidate reagent for differential hemolysis has been identified in the above defined method that is based on a 1 in 20 dilution of a whole blood sample in a candidate hemolysis reagent, another ratio of whole blood sample to an adjusted hemolysis reagent can be used as required.

In case the analyte of interest is expected to be highly concentrated in the blood sample under investigation, the concentration of the hemolysis reagent can stay the same as identified in the above setting and lower ratios of whole blood to hemolysis reagent, e.g., 1:30, 1:40 or 1:50 can be used.

Preferably the hematolytically active chemical in reagent for differential hemolysis is used in at least the minimal concentration sufficient to achieve differential hemolysis as determined above.

In case the analyte of interest is present in rather a low concentration it may be necessary not to dilute the whole blood sample 1:20 but less. This is feasible by adjusting the concentration of the hemolysis reagent accordingly, such that the final relative concentration of hemolysis reagent to whole blood in the mixture of the hemolysis reagent and the whole blood sample stays the same as the ratio identified for the required minimal concentration of hemolysis reagent as determined in the above described assessment. The maximal concentration is the highest possible concentration of the candidate hemolysis reagent leading to a differential hemolysis but not causing precipitation of sample constituents as assessed in the above described setting.

By way of example: It has been found that 1-Methyl-1-octyl pyrrolidiniumchloride/KSCN if used in a final concentration of 1% and 0.4%, respectively, is appropriate to achieve the desired result, i.e., the differential hemolysis of a whole blood sample at a final dilution of 1:20. Dilution of an analyte in the processed blood sample can be reduced if for example the concentration of this hemolysis reagent is adjusted to 2% for 1-Methyl-1-octyl pyrrolidiniumchloride and 0.8% for KSCN, respectively. This adjusted hemolysis reagent if later mixed 1:1 with a 1:5 diluted whole blood sample also leads to differential hemolysis of the whole blood sample, since the ratio of whole blood to hemolysis reagent is kept constant. If 1 ml of a hemolysis reagent comprising 10% of 1-Methyl-1-octyl pyrrolidiniumchloride and 4% of KSCN, respectively, is mixed with 1 ml of whole blood diluted 1:1 in PBS hemolysis is also observed. Alternatively 1 ml of whole blood could be added to 2 ml of a hemolysis reagent comprising 10% of 1-Methyl-1-octyl pyrrolidiniumchloride and 4% of KSCN, respectively.

For many routine applications it is expected that the ideal ratio of whole blood sample to a hemolysis reagent will be between 10:1 and 1:20. Preferably in a method according to the present invention the sample of whole blood is mixed with the hemolysis reagent at a ratio from 5 to 1 to 1 to 15. More preferred the ratio is between 2 to 1 and 1 to 10, also preferred between 1 to 1 and 1 to 5. The final, i.e., highest possible concentration of an adjusted hemolysis reagent used in the clinical routine will depend on the solubility and also the price of such reagent.

In case 1-Butyl-4-methylpyridinium tetrafluoroborate or 1-Butyl-3-methyl-imidazolium tetrafluoroborate, respectively, is used as the sole membrane-solubilizing chemical in a reagent for differential hemolysis, the sampling tube according to the present invention preferably comprises it in a concentration of 10 to 30%, also preferred are concentrations from 12 to 25%.

In case 1-Butyl-3-methyl-imidazoliumoctylsulfate is used as the sole membrane-solubilizing chemical in a reagent for differential hemolysis, the sampling tube according to the present invention preferably comprises it in a concentration of 1 to 30%, also preferred are concentrations from 2 to 10%.

In case 1-Butyl-3-methylpyridinium is used as a cation in a reagent for differential hemolysis, it is preferably used together with iodide or rhodanide as an anion and the sampling tube according to the present invention preferably comprises 1-Butyl-3-methylpyridinium in a concentration of 5 to 30%, also preferred in concentrations from 10 to 25%.

In case 1-Hexylpyridiniumchloride is used as the sole membrane-solubilizing chemical in a reagent for differential hemolysis, the sampling tube according to the present invention preferably comprises it in a concentration of 15 to 30%, also preferred are concentrations from 20 to 25%.

In case 1-Hexylpyridiniumchloride in combination with an equimolar concentration of KSCN are used as the membrane-solubilizing chemicals in a reagent for differential hemolysis, the sampling tube according to the present invention preferably comprises 1-Hexylpyridiniumchloride in a concentration of 4 to 30%, also preferred are concentrations from 5 to 20%.

In case 1-Methyl-1-octyl pyrrolidiniumchloride is used as the sole membrane-solubilizing chemical in a reagent for differential hemolysis, the sampling tube according to the present invention preferably comprises it in a concentration of 5 to 30%, also preferred are concentrations from 10 to 25%.

In case 1-Methyl-1-octyl pyrrolidiniumchloride in combination with an equimolar concentration of KSCN is used in a reagent for differential hemolysis, the sampling tube according to the present invention preferably comprises the 1-Methyl-1-octyl pyrrolidiniumchloride in a concentration of 1 to 30%, also preferred are concentrations from 1 to 20%, as well as from 1 to 10 or from 1 to 5%.

In case N-Octylpyridiniumchloride is used as the sole membrane-solubilizing chemical in a reagent for differential hemolysis, the sampling tube according to the present invention preferably comprises it in a concentration of 10 to 30%, also preferred are concentrations from 10 to 25%.

In case 3-Carbamoyl-1-octyloxymethylpyridiniumchloride is used as the sole membrane-solubilizing chemical in a reagent for differential hemolysis, the sampling tube according to the present invention preferably comprises it in a concentration of 0.5 to 30%, also preferred are concentrations from 0.75 to 25%, as well as from 1 to 10 or from 1 to 5%.

Further preferred chemicals for differential hemolysis for use in a hemolysis tube according to the present invention are 1-Hexylpyridinium cations in combination with SCN⁻ anions, 1-Methyl-1-octyl pyrrolidinium cations in combination with SCN anions, and 3-Carbamoyl-1-octyloxymethyl pyridinium cations.

Preferably the chemical used for differential hemolysis comprised in the ready-to-use tube of the present invention is used at a concentration of no more than 50% weight/volume, also preferred at no more than 30%, or also preferred at no more than 25 or 20% weight/volume.

Differential hemolysis is accompanied by the release of intra-cellular constituents like proteins, including proteases. In certain applications, like detection of proteins, it will be advantageous to block the activity of enzymes, e.g., of proteases. In a preferred embodiment the sampling tube according to the present invention will contain a reagent for differential hemolysis that also comprises an enzyme inhibitor. Preferably the enzyme inhibitor is a protease inhibitor.

There is an ever increasing number of proteases and also of corresponding protease inhibitors from which an appropriate protease inhibitor may be selected as required. One important class of proteases are the so-called serine proteases that have the amino acid serine in their active site. Well-known examples of serine proteases are trypsin, chymotrypsin, kallikrein, and urokinase. The skilled artisan is familiar with the fact that certain protease inhibitors are active against serine proteases. The inhibitory potential of such proteases and their activity spectrum is, e.g., described in the data sheets from commercial suppliers, like Serva, Heidelberg, or Roche Diagnostics GmbH, Mannheim. Preferably the serine protease inhibitor is selected from the group consisting of AEBSF-HCl (e.g., Serva Cat. No. 12745), APMSF-HCl (e.g., Serva Cat. No. 12320), aprotinin (e.g., Roche Diagnostics, Cat. No. 10 981 532 001), chymostatin (e.g., Roche Diagnostics, Cat. No. 11 004 638 001), Pefabloc® SC (e.g., Roche Diagnostics, Cat. No. 11 585 916 001), and PMSF (e.g., Roche Diagnostics, Cat. No. 10 837 091 001).

A further important class of proteases are the so-called cysteine proteases that have the amino acid cysteine in their active site. Well-known examples of cysteine proteases are papain and calpain. The skilled artisan is familiar with the fact that certain protease inhibitors are active against cysteine proteases. Some of these inhibitors are also active against serine proteases, e.g., PMSF may be used as an inhibitor of cysteine proteases as well as an inhibitor of serine proteases. The inhibitory potential of such proteases and their activity spectrum is, e.g., described in the data sheets from commercial suppliers, like Serva, Heidelberg, or Roche Diagnostics GmbH, Mannheim. Preferably the cysteine protease inhibitor is selected from the group consisting of leupeptine (e.g., Roche Diagnostics, Cat. No. 11 034 626 001), PMSF (see above), and E-64 (e.g., Roche Diagnostics, Cat. No. 10 874 523 001).

A further important class of proteases are the so-called metalloproteases. Metalloproteases are characterized by containing a metal ion, e.g., $Zn^{2+}$, $Ca^{2+}$ or $Mn^{2+}$ in the active center. Well-known examples of metalloproteases are digestive enzymes such as carboxypeptidases A and B and thermolysin. The skilled artisan is familiar with the fact that certain protease inhibitors are active against metalloproteases. Metalloproteases are most easily inactivated by substances binding to the metal ion and forming a metal chelate complex therewith. Preferably ethylene-diaminotetra acetic acid (EDTA), ethyleneglycol bis(aminoethylether)tetra acetic acid (EGTA), and/or 1,2-diaminocyclohexane-N,N,N',N'-tetra acetic acid (CDTA) are used to inactivate metalloproteases. Other appropriate inhibitors of metalloproteases are Phosphoramidon (=N-(α-Rhamnopyranosyloxyhydroxy phosphinyl)-L-leucyl-Ltryptophan, disodium salt; e.g., Roche Diagnostics Cat. No. 10 874 531 001) and bestatin (e.g., Roche Diagnostics Cat. No. 10 874 515 001). The inhibitory potential of these protease inhibitors and their activity spectrum is, e.g., described in the corresponding data sheets from commercial suppliers, like Serva, Heidelberg, or Roche Diagnostics GmbH, Mannheim. Preferred inhibitors of metalloproteases are EDTA, EGTA and/or bestatin.

A further important class of proteases is known as aspartic (acidic) proteases. Aspartic proteases are characterized by having an aspartic acid residue in the active center. Well-known examples of aspartic proteases are pepsin, cathepsin D, chymosin, and renin. The skilled artisan is familiar with the fact that certain protease inhibitors are active against aspartic proteases. Preferred inhibitors of aspartic acid proteases are α2-macroglobulin (e.g., Roche Diagnostics Cat. No. 10 602 442 001) and pepstatin (e.g., Roche Diagnostics Cat. No. 11 359 053 001).

For certain applications it will be possible to use a reagent for differential hemolysis comprising a protease inhibitor for a certain class of proteases.

It represents a preferred embodiment according to the present invention that a cocktail of two or more protease inhibitors is used to inhibit unwanted degradation of a proteinaceous analyte in a differentially hemolyzed blood sample. Preferably the reagent for differential hemolysis used in a sampling tube according to the present invention will comprise at least two different protease inhibitors with activity against two classes of proteases selected from the group consisting of serine proteases, cysteine proteases, metalloproteases and aspartic proteases. Also preferred at least three of these enzyme classes will be inhibited by an appropriate inhibitor cocktail. Preferably the stool sample diluent according to the present invention will contain a protease inhibitor cocktail that is composed of protease inhibitors that are active against serine proteases, cysteine proteases, metalloproteases and aspartic proteases, respectively.

Preferably 10 or less different protease inhibitors will be used and will suffice to achieve sufficient protease inhibition in order to stabilize a proteinaceous analyte of interest in a differentially hemolyzed blood sample.

Preferably the protease inhibitor is selected from the group consisting of aprotinin, chymostatin, leupeptine, EDTA, EGTA, CDTA, pepstatin A, phenylmethyl sulfonylfluoride (PMSF), and Pefabloc® SC. Preferably the protease inhibitor additionally comprised in the reagent for differential hemolysis will contain one or more of the protease inhibitors chymostatin, leupeptine, CDTA, pepstatin A, PMSF, and Pefabloc® SC. Also preferred it will contain aprotinin, leupeptine, EDTA and Pefabloc® SC.

In a further preferred embodiment the sampling tube according to the present invention contains a chemical for differential hemolysis and an anti-coagulant, as described above, and additionally comprises a nuclease. Long term storage or transport of a differentially hemolyzed blood sample may be accompanied by release of nucleic acids, especially DNA may be released from the nuclei of eukaryotic blood cells. In case a significant amount of DNA would be set free this would lead to a high viscosity of the sample and such sample could no longer be used in diagnostic routine. This effect can be counteracted by use of a nuclease. Preferably the sampling tube according to the present invention contains a reagent for differential hemolysis that comprises a DNase. A preferred DNase is benzonase.

In a preferred embodiment the present invention relates to the use of a ready-to-use and single-use sampling tube sampling tube comprising a chemical for differential hemolysis and an anti-coagulant in the processing of a whole blood sample for liquid chromatography. The embodiments described above as preferred for the sampling tube and the reagent for differential hemolysis contained therein also apply to the use of such sampling tube in the processing of a whole blood sample for liquid chromatography.

Liquid chromatography (LC) is an extremely important analytical technique which is used for the separation, identification and quantization of an analyte of interest even if present in a complex mixture of different sample constituents. During LC the chemical components in a mixture are carried through a stationary phase by the flow of a liquid mobile phase. Separation in liquid chromatography is achieved by means of differences in the interactions of the analytes with both the mobile and stationary phases. As the skilled artisan appreciates both a stationary phase and a mobile phase appropriate to the analytes under investigation have to be chosen. In addition, the user will identify chromatographic conditions appropriate to maintain the sharpness of analyte bands as a sample moves through the stationary phase column to the detector.

High Performance Liquid Chromatography, also known as High Pressure Liquid Chromatography, abbreviated as HPLC, is a special form of liquid chromatography and nowadays used frequently in biochemistry and analytical chemistry. The analyte is forced through a column of the stationary phase in a liquid (mobile phase) at high pressure, which decreases the time the separated components remain on the stationary phase and thus the time they have to diffuse within the column. This leads to narrower peaks in the resulting chromatogram and thence to better resolution and sensitivity as compared to LC.

The mobile phase is chosen to ensure solubility of the sample solutes. For the stationary phase, preferably microparticulate silica (bare or chemically modified) is used, because its high surface area accentuates the differences in solute-stationary phase interactions. The use of a stationary phase that interacts strongly with solutes relative to solute mobile-phase interactions will result in very long retention times, a situation which is not analytically useful. Hence the stationary phase must be selected so as to provide weak to moderate solute interactions relative to those in the mobile phase. As a consequence, the nature of the solute governs the type of LC selected. The stronger interactions should occur in the mobile phase to ensure sample solubility and ready elution, while the stationary phase should be responsive to more subtle differences among the solutes. For example, polar neutral compounds are usually better analyzed using a polar mobile phase together with a nonpolar stationary phase that distinguishes subtle differences in the dispersive character of the solutes. One of the powerful aspects of HPLC is that the mobile phase can be varied to alter the retention mechanism. Modifiers can be added to the mobile phase to control retention. For example, pH is an important variable in aqueous mobile phases.

Five general classes of LC can be distinguished:

1. Normal-phase chromatography calls for the use of a polar stationary phase in conjunction with a non-polar (dispersive) mobile phase.
2. Reverse-phase chromatography, the opposite possibility, calls for the use of a non-polar stationary phase and a polar mobile phase (composed of one or more of the solvents water, methanol, acetonitrile, and tetrahydrofuran).
3. Ion-exchange chromatography involves ionic interactions. In this case the mobile phase must support ionization to ensure solubility of ionic solutes. The stationary phase must also be partially ionic to promote some retention. Consequently, the interactions with the stationary phase are strong, and this is usually reflected in longer analysis times and broad peaks.
4. Size-Exclusion chromatography involves separations based on molecular size alone and ideally requires that there be no energetic interaction of the solutes with the stationary phase.
5. Affinity chromatography is based on a specific interaction, e.g., between the members of a specific binding pair, like antigen and corresponding antibody or receptor and corresponding ligand. For example a first partner of a binding pair is bound to an appropriate stationary phase and used to capture the second partner of the binding pair. The second partner can be released and isolated by appropriate means.

In routine applications the stationary phase, the so-called bed material, e.g., alkylsilanol coated porous silica particles in an RP-HPLC-application, is packed into an appropriate column. The diameter of the stationary phase particles is usually in the range of 1 to 10 µm for the majority of HPLC applications, the average pore size of these particles varies from a few nanometers to hundreds of nanometers. Non-porous particles are also used in some HPLC applications. In addition, so-called monolithic materials may also be used in the HPLC applications. The small particles of the stationary phase material necessitate the high pressure used in HPLC. The bed material usually is protected by a frit. Typical frits have a pore size of 1 µm, 0.45 µm or 0.2 µm. The smaller the particles the smaller is usually the pore size of the frit. If a sample comprises a constituent capable of blocking an HPLC frit this is detrimental for any routine analysis.

A whole blood sample, as well as an "over-treated" whole blood sample comprising precipitates of sample constituents causes a rapid blocking of any routine HPLC frit or column. As the skilled artisan will appreciate blocking of the frit used in an HPLC column will occur the more rapidly the lower the pore size of the frit, the smaller the diameter of the stationary phase particles and the smaller the column diameter. In case the frit would not be selected appropriately, i.e., a too large pore size, the particle size of the column material would also matter and the column itself would block more rapidly the smaller the particles are.

By sampling a whole blood sample directly into a sampling tube according to the present invention a processed whole blood sample is obtained that can be applied directly to an HPLC column, without running the risk of blocking the column. In a preferred embodiment the present invention relates to a method of collecting a blood sample into a ready-to-use sampling tube according to the present invention, thereby processing the whole blood sample to a differentially hemolyzed blood sample and thereafter subjecting said processed blood sample to an HPLC step.

Preferably, the stationary phase particles used in such HPLC step are in the range of 1 to 10 µm, also preferred in the range of 2 to 7 µm in diameter. Preferably the frit used in such HPLC step has a pore size of 0.45 µm or also preferred of 0.2 µm.

In a further preferred embodiment the present invention relates to the use of a differentially hemolyzed blood sample obtained by collecting whole blood into a sampling tube according to the present invention in a liquid chromatography-based analysis of an analyte of interest.

The analyte of interest can be detected by any appropriate means. Appropriate and preferred detectors sense the presence of a compound passing through, and provide an electronic signal to a recorder or computer data station. The output is usually in the form of a chromatogram and a substance of interest is usually found in a certain peak. The peak area or peak height can be used to quantify the amount of analyte present in the sample investigated.

The detector for an HPLC system is the component that emits a response due to the eluting sample compound and subsequently signals a peak on the chromatogram. It is positioned immediately posterior to the stationary phase in order to detect the compounds as they elute from the column. The detection and sensitivity parameters may be controlled by the skilled artisan. There are many types of detectors that can be used with HPLC. Some of the more common detectors include: Refractive Index (RI), Ultra-Violet (UV), Fluorescent, Radiochemical, Electrochemical, Near-Infra Red (Near-IR), Mass Spectroscopy (MS), Nuclear Magnetic Resonance (NMR), and Light Scattering (LS).

Refractive Index (RI) detectors measure the ability of sample molecules to bend or refract light. This property for each molecule or compound is called its refractive index. For most RI detectors, light proceeds through a bi-modular flow-cell to a photodetector. One channel of the flow-cell directs the mobile phase passing through the column while the other directs only the mobile phase. Detection occurs when the light is bent due to samples eluting from the column, and this is read as a disparity between the two channels.

Fluorescent detectors measure the ability of a compound to absorb and then re-emit light at given wavelengths, respectively. Each compound able to emit the fluorescence light has a characteristic excitation and emission wavelength. The excitation light passes through the flow-cell while the photodetector in orthogonal position measures the emitted light at specific wavelength.

Radiochemical detection involves the use of radiolabeled material, usually tritium (3H) or carbon-14 (14C). It operates by detection of fluorescence associated with beta-particle ionization, and it is most popular in metabolite research.

Electrochemical detectors measure compounds that undergo oxidation or reduction reactions. This is usually accomplished by measuring gain or loss of electrons from migrating samples as they pass between electrodes at a given difference in electrical potential.

Mass spectrometry is an analytical technique used to measure the mass-to-charge ratio (m/z (or m/q)) of ions. It is most generally used to analyze the composition of a physical sample by generating a mass spectrum representing the masses of sample components. The technique has several applications, including: identifying unknown compounds by the mass of the compound and/or fragments thereof; determining the isotopic composition of one or more elements in a compound; determining the structure of compounds by observing the fragmentation of the compound; quantitating the amount of a compound in a sample using carefully designed methods (mass spectrometry is not inherently quantitative); studying the fundamentals of gas phase ion chemistry (the chemistry of ions and neutrals in vacuum); determining other physical, chemical or even biological properties of compounds with a variety of other approaches.

A mass spectrometer is a device used for mass spectrometry, and produces a mass spectrum of a sample to analyze its composition. This is normally achieved by ionizing the sample and separating ions of differing masses and recording their relative abundance by measuring intensities of ion flux. A typical mass spectrometer comprises three parts: an ion source, a mass analyzer, and a detector.

The kind of ion source is a contributing factor that strongly influences what types of samples can be analyzed by mass spectrometry. Electron ionization and chemical ionization are used for gases and vapors. In chemical ionization sources, the analyte is ionized by chemical ion-molecule reactions during collisions in the source. Two techniques often used with liquid and solid biological samples include electrospray ionization (ESI) and matrix-assisted laser desorption/ionization (MALDI). Other techniques include fast atom bombardment (FAB), thermospray, atmospheric pressure chemical ionization (APCI), secondary ion mass spectrometry (SIMS) and thermal ionisation.

In a preferred embodiment the detecting of an analyte in a method according to the present invention is performed by mass spectroscopy.

Nuclear magnetic resonance (NMR) detection is based on the fact that certain nuclei with odd-numbered masses, including H and $^{13}C$, spin about an axis in a random fashion. However, when placed in a strong magnetic field, the spins are aligned either parallel or anti-parallel to the magnetic field, with the parallel orientation favored since it is slightly lower in energy. These magnetic nuclei can absorb RF energy when placed in a magnetic field of a specific strength. When this absorption occurs, the nucleus is said to be on resonance. Interestingly for analytical scientists, different atoms within a molecule resonate at different frequencies at a given field strength. The observation of the resonance frequencies of a molecule allows a user to discover structural information about the molecule.

When a source emits a parallel beam of light which strikes particles in solution, some light is reflected, absorbed, transmitted, or scattered. These phenomena can be measured by a light-scattering (LS) detector. The most prominent forms of LS detection are termed nephelometry and turbidometry. Nephelometry is defined as the measurement of intensity of scattered light emanated from an illuminated volume of a suspension. The ratio of scattered intensity to illuminating intensity is compared with a standard of known properties. Turbidometry is defined as the measure of the reduction of light transmitted due to particles in solution. It measures the light scatter as a decrease in the light that is transmitted through the particulate solution. Therefore, it quantifies the residual light transmitted.

Near-infrared detectors operate by scanning compounds in a spectrum from 700 to 1100 nm. Stretching and bending vibrations of particular chemical bonds in each molecule are detected at certain wavelengths.

In a preferred embodiment according to the present invention a whole blood sample derived from a mammal or a sample of anti-coagulated whole blood derived from a mammal will be collected into the ready-to-use sampling tube according to the present invention and the analyte of interest comprised in the processed sample obtained thereby will be detected online, i.e., without any additional step like filtration, precipitation or centrifugation. In a preferred embodiment the present invention therefore relates to method of analyzing a sample of whole blood, comprising the steps of collecting the sample into a ready-to-use sampling tube according to the present invention, obtaining a differentially hemolyzed whole blood sample, subjecting this processed sample to an HPLC step and thereby or thereafter detecting an analyte of interest in said sample.

An analyte according to the present invention may be any inorganic or organic molecule, including a biomolecule. Preferably the analyte will not be a nucleic acid, especially it will not be a DNA. Preferably the analyte is selected from the group consisting of a polypeptide, a carbohydrate, and an inorganic or organic drug molecule. Preferably the analyte of interest has an MW of 10,000 Da or less, also preferred of 9 kDa or less, of 8 or less, of 7 kDa or less, of 6 kDa or less, or of 5 kDa or less, respectively.

A polypeptide or protein is a molecule that is essentially composed of amino acids and that has at least two amino acids linked by peptidic linkage. In case the analyte of interest to be investigated in a method disclosed here, the polypeptide preferably will consist of at least 3, 4, 5, 6, 7, 8, 9, 10, 12, 15, 20, 25, and 30 to up to about 100 amino acids. Preferably the polypeptide will contain from 5 to 100, also preferred from 10 to 40 amino acids. Suitable peptidic analytes of interest are, e.g., peptide hormones, and other polypeptides present in the circulation and especially polypeptides released from red blood cells, e.g., due to incubating a sample of whole blood in a sampling tube as disclosed herein.

Preferably the method according to the present invention is used in the online detection of an analyte from a whole blood sample wherein said analyte is at least partially located inside a red blood cell.

A preferred target analyte according to the present invention is selected from the group consisting of the drugs of abuse and the immunosuppressive drugs.

Preferred target analytes are the drugs of abuse. The drug of abuse is preferably selected from the group consisting of amphetamine, cocaine and cocaine metabolites like benzoyleegnonine, methamphetamine, opiate and opiate derivatives, camabinoids like tetrahydrocannabinol, and phencyclidine.

Preferred target analytes are immunosuppressive drugs. The immunosuppressive drug is preferably selected from the group consisting of cyclosporine (CsA), mycophenolate mofetil (MMF), rapamycin (RAPA also known as sirolimus), tacrolimus (FK-506) azathioprine (AZA), and methylprednisolone (MP).

A further preferred target analyte is folate, especially the total folate as comprised in both the blood plasma and in the red blood cells.

Preferred analytes to be measured from a whole blood sample collected into a sampling tube according to the present invention are sirolimus, tacrolimus and folate.

In a further embodiment the present invention relates the use of a sampling tube containing a reagent for differential hemolysis of a whole blood sample, wherein said reagent for differential hemolysis comprises a hematolytically active chemical and an anti-coagulant, and wherein said sampling tube is a ready-to-use and single-use sampling tube in the processing of a whole blood sample for liquid chromatography. The embodiments described above as preferred with regard to the reagent for differential hemolysis contained in the sampling tube according to the present invention also apply to the use of the hemolysis reagent in the processing of a whole blood sample for liquid chromatography.

The single-use and ready-to-use sampling tube for a whole blood sample according to the present invention and its use in a routine diagnosis environment has the striking advantage that the whole blood sample upon sampling is directly processed into a differentially hemolyzed blood sample. This obviates the measures of precaution otherwise required for handling and storing of a whole blood sample or of an anti-coagulated whole blood sample. The differentially hemolyzed blood can be handled like a plasma or serum sample. No cells can settle out and no gradual increase in hemolysis that may interfere with a correct analyte measurement can occur anymore. Transport of a differentially hemolyzed blood sample is easy and convenient. A virus particle, if present, should also be solubilized and destroyed if brought into contact with a reagent for differential hemolysis. Though not tested it is therefore expected that even the biohazard risk will be largely reduced by use of a whole blood sampling tube according to the present invention.

The following examples and figures are provided to aid the understanding of the present invention, the true scope of which is set forth in the appended claims. It is understood that modifications can be made in the procedures set forth without departing from the spirit of the invention.

EXAMPLE 1

Evaluation of Various Candidate Hemolysis Reagents

Example 1.1

Visual Evaluation of Hemolysis

Solution A: Fresh EDTA-stabilized whole blood is diluted with 0.15 molar sodium chloride solution in the ratio 1:10 (50 µL EDTA-blood plus 450 µL sodium chloride solution).

Solution B: A solution of the candidate hemolysis reagent in 0.15 molar sodium chloride is prepared wherein the concentration of the hemolysis reagent is twice as high as the desired final concentration in the hemolysate, e.g., to get a final concentration of 25% of 1-Butyl-4-methylpyridinium tetrafluoroborate a solution of 50% (50 mg salt plus 50 mL 0.15 molar sodium chloride in water) is prepared. In the case of the addition of a second anion, e.g., iodine (1-Butyl-3-methylpyridiniumchloride/KJ) the stated salt is added in an equimolar amount.

Hemolysate is prepared by mixing solution A and B in equal volumes, e.g., 500 µL solution A plus 500 µL solution B.

After mixing the hemolysate is inspected visually for turbidometry and clearness immediately after mixing, after 1 minute, 2, 5, 6, 7, 20 and 40 minutes. The time until a clear solution is observed is recorded.

TABLE 1

Visual evaluation of candidate reagents for differential hemolysis

| Hemolysis reagent | final concentration (weight/volume) | clear after (min.) |
|---|---|---|
| 1-Butyl-4-methylpyridinium tetrafluoroborate | 25% | 20 min. |
| 1-Butyl-4-methylpyridinium tetrafluoroborate | 12.5% | 40 min. |
| 1-Butyl-4-methylpyridinium tetrafluoroborate | 6% | Turbid |
| 1-Butyl-3-methyl-imidazolium tetrafluoroborate | 25% | 20 min. |
| l-Butyl-3-methyl-imidazoliumoctylsulfate | 25% | immediately |
| 1-Butyl-3-methyl pyridiniumchloride | 25% | turbid |
| 1-Butyl-3-methyl pyridiniumchloride/KJ | 25%/22% | 20 min. |
| 1-Butyl-3-methyl pyridiniumchloride/KSCN | 25%/13% | 5 min. |

TABLE 1-continued

Visual evaluation of candidate reagents for differential hemolysis

| Hemolysis reagent | final concentration (weight/volume) | clear after (min.) |
|---|---|---|
| 1-Hexylpyridiniumchloride/KSCN | 25%/12% | immediately |
| 1-Hexylpyridiniumchloride/KSCN | 12.5%/6% | 1 min. |
| 1-Hexylpyridiniumchloride/KSCN | 6.25%/3% | 6 min. |
| 1-Hexylpyridiniumchloride/KSCN | 3.12%/1.5% | turbid |
| 1-Hexylpyridiniumchloride | 25% | 7 min. |
| 1-Hexylpyridiniumchloride | 12.5% | turbid |
| 1-Methyl-1-octyl pyrrolidiniumchloride/KSCN | 25%/10% | immediately |
| 1-Methyl-1-octyl pyrrolidiniumchloride/KSCN | 12.5%/5% | immediately |
| 1-Methyl-1-octyl pyrrolidiniumchloride/KSCN | 6.25%/2.5% | immediately |
| 1-Methyl-1-octyl pyrrolidiniumchloride/KSCN | 3.12%/1.25% | immediately |
| 1-Methyl-1-octyl pyrrolidiniumchloride/KSCN | 2.5%/1% | immediately |
| 1-Methyl-1-octyl pyrrolidiniumchloride/KSCN | 1.25%/0.5% | 2 min. |
| 1-Methyl-1-octyl pyrrolidiniumchloride/KSCN | 0.62%/0.25% | turbid |
| 1-Methyl-1-octyl pyrrolidiniumchloride | 25% | immediately |
| 1-Methyl-1-octyl pyrrolidiniumchloride | 2.5% | turbid |
| N-Octylpyridiniumchloride | 25% | 2 min. |
| 3-Carbamoyl-1-octyloxymethyl pyridiniumchloride | 12.5% | immediately |
| 3-Carbamoyl-1-octyloxymethyl pyridiniumchloride | 6.25% | immediately |
| 3-Carbamoyl-1-octyloxymethyl pyridiniumchloride | 1.5% | immediately |

As is obvious from the above table, by visual assessment good candidate reagents for differential hemolysis can be identified visually.

Example 1.2

Microscopic Evaluation of Hemolysis

Solution A: Fresh EDTA-stabilized whole blood is diluted with 0.15 molar sodium chloride solution in the ratio 1:10 (50 µL EDTA-blood plus 450 µL sodium chloride solution).

Solution B: A solution of the hemolysis reagent in 0.15 molar sodium chloride is prepared where the concentration of the hemolysis reagent is twice as high as the desired final concentration in the hemolysate, e.g., to get a final concentration of 25% of 1-Butyl-4-methylpyridinium tetrafluoroborate a solution of 50% (50 mg salt plus 50 mL 0.15 molar sodium chloride in water) is prepared. In the case of the addition of a second anion, e.g., iodine (1-Butyl-3-methylpyridiniumchloride/KJ) the stated salt is added in an equimolar amount.

Hemolysate is prepared by mixing solution A and B in equal volumes, e.g., 20 µL solution A plus 20 µL solution B May-Grünwald Staining and Microscopy:

After mixing of the hemolysate a droplet is smeared on a microscope slide, air dried at room temperature and stained with May-Grünwald staining reagent (Merck Cat. No. 1.01424 May-Grünwald's Eosin Methylene Blue Solution). After May-Grünwald-staining nuclei stain to varying shades of purple, cytoplasm is seen in tones of blue to light pink, fine reddish to lilac granules may be present in cytoplasm of some cell types, basophiles will demonstrate dark blue black granules in the cytoplasm, eosinophils will demonstrate bright orange granules in the cytoplasm, and red blood cells are stained pink to orange.

Microscopy is performed by oil immersion light microscopy (magnification ×630).

Figure 2:
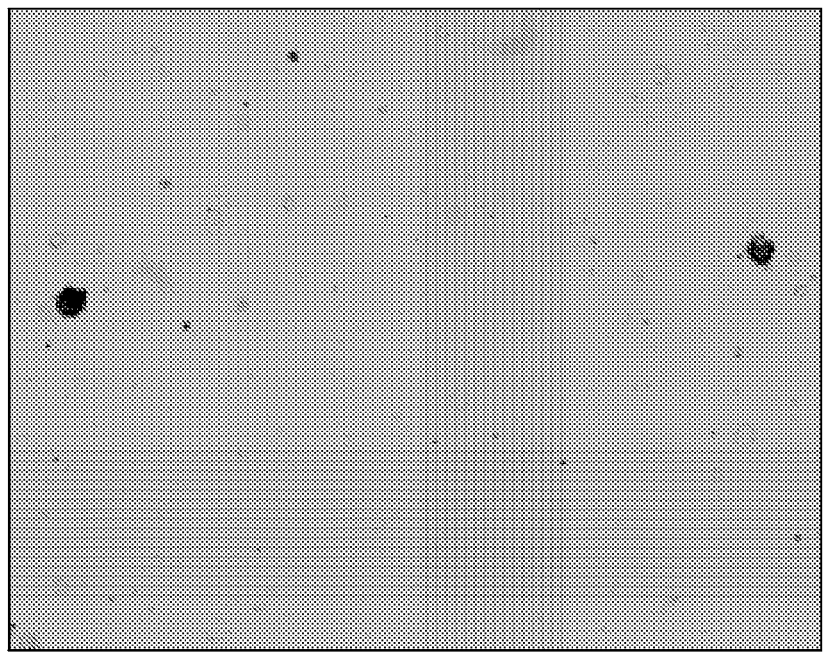
FIG. 2: Light microscopy of a 1 in 10 diluted whole blood hemolyzed with 1-Butyl-4-methylpyridinium tetrafluoroborate (25%). May-Grünwald staining has been applied. No erythrocytes or membranes are left, nuclei are still intact.

Comparative results—FIG. 1 lysate obtained by water and FIG. 2 lysate obtained with a reagent appropriate for differential hemolysis, respectively—show that the addition of an appropriate hemolyzing reagent within a few minutes will lead to complete lysis of erythrocytes.

Trypane Blue Staining and Microscopy:

The processed whole blood sample is mixed (1:1) with Trypane blue solution (Merck cat. no. 1.11732; Trypanblau C.I. 23850) and dispensed into a Neugebauer-chamber for microscopy. Microscopy is performed by oil immersion light microscopy (magnification ×630).

Figure 3:
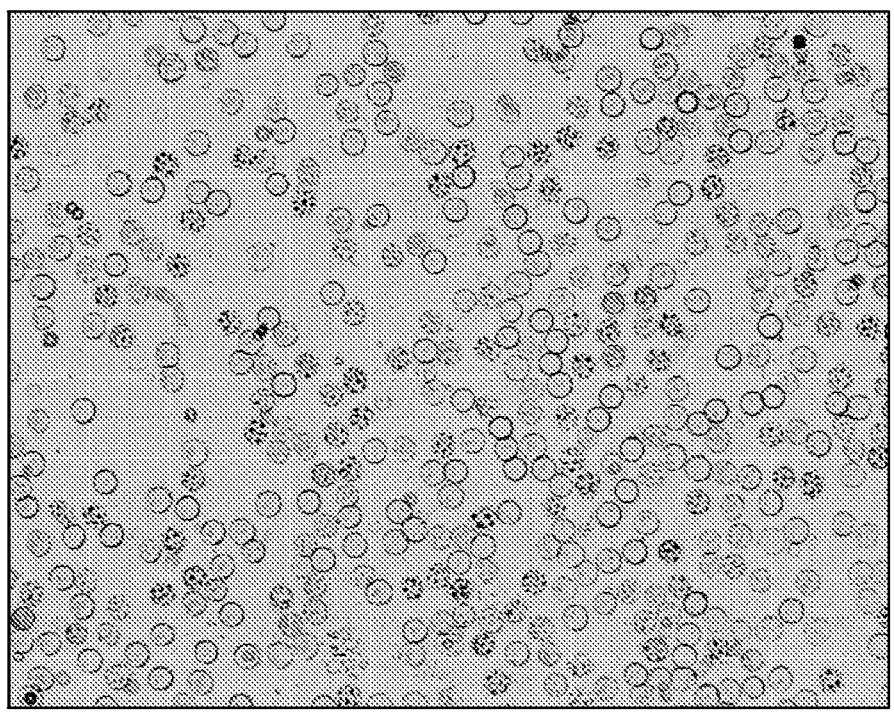
FIG. 3: Light microscopy of a 1 in 10 diluted whole blood hemolyzed with water. Trypane blue staining has been used.
Figure 4A:
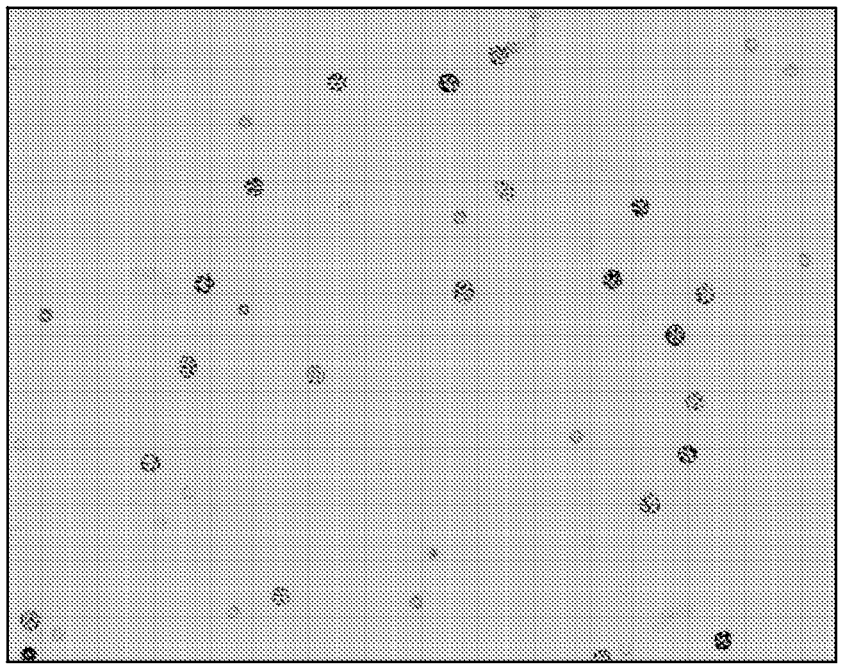
FIG. 4: Light microscopy of a 1 in 10 diluted whole blood hemolyzed with 1-Butyl-4-methylpyridinium tetrafluoroborate (25%). Trypane blue staining has been used. a) 2.5 min incubation time: Only few residual erythrocytes are left b) 15 min incubation time: No erythrocytes or membranes are left.
Figure 4B:
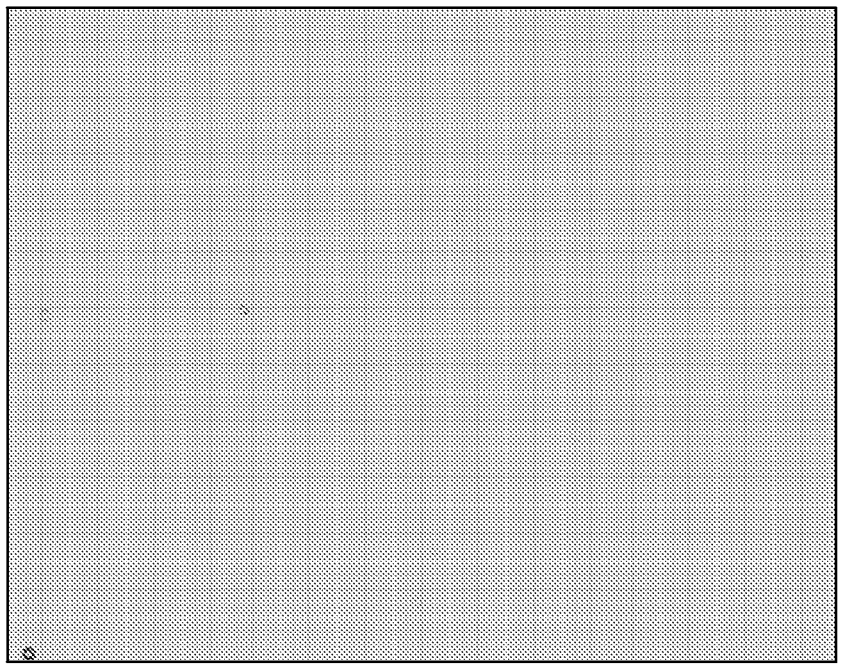
Figure 5:
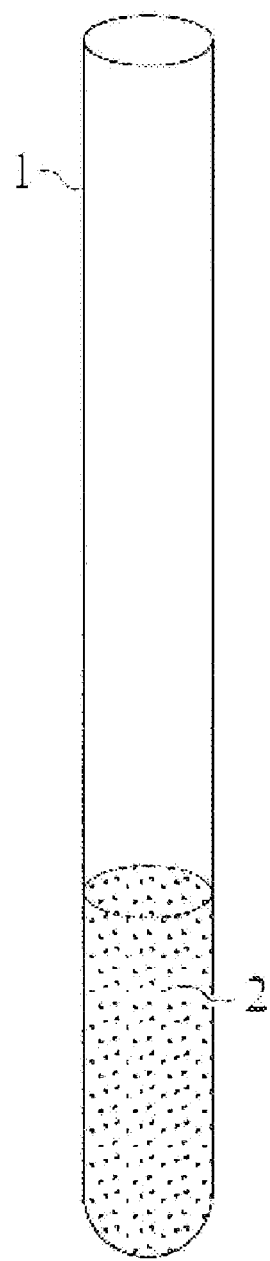
FIG. 5: Sampling tube (1) containing differential hemolysis reagent (2).

Comparative results—FIG. 3 lysate obtained by water and FIGS. 4a) and b) lysates obtained with a reagent appropriate for differential hemolysis, respectively—show that the addition of an appropriate hemolyzing reagent within a few minutes will lead to complete lysis of erythrocytes.

EXAMPLE 2

Evaluation of Various Candidate Hemolysis Reagents by HPLC

To assess lysis efficiency a hemolyzed whole blood sample prepared according Example 1 is injected into a HPLC system and the backpressure of the system is monitored.

The HPLC system consists of an HP 1090 liquid chromatograph (Agilent) with a DR 5 solvent delivery system, a thermostat equipped auto sampler and an auto injector. Lysis efficacy is assessed by applying 50 times 10 µL of the treated whole blood sample to an HPLC column having 5 µm Symmetry C18 particles as bed material, an inner column diameter of 2 mm, column length of 20 mm and a frit with 0.5 µm pore size. The eluent is a gradient from water with 0.1% formic acid to acetonitrile with 0.1% formic acid within 5 minutes and at a flow rate of 0.2 mL/min. The observed increase of back pressure over 50 injections is less than 20 bar.

If lysis is achieved with distilled water only, the observed increase of back pressure under the above HPLC conditions is more than 100 bar.

EXAMPLE 3

Processing of EDTA-Anticoagulated Whole Blood by Pipetting it into a Tube Comprising a Reagent for Differential Hemolysis and by Gently Shaking the Mixture 3.1 1-Butyl-4-methylyridinium tetrafluoroborate The lysis reagent is prepared by mixing 11.25 mL potassiumthiocyanate solution (0.1 molar; i.e., 9.72 gram KSCN dissolved in 1 litre distilled water) with 12.5 mL 1-Butyl-4-methylpyridinium tetrafluoroborate (BMPBF4) and 23.7 mL sodium chloride (0.15 molar in water). This reagent for differential hemolysis thus has a concentration of about 25% BMPBF4. Potassium thiocyanate is present in a much lower molar concentration and thus most likely does not significantly contribute to the effects observed.

250 microliter of EDTA-anticoagulated whole blood is pipetted into a vial containing 5 milliliter of this lysis reagent. For hemolysis the content of the tube is gently mixed by shaking. An optically clear lysate is obtained within five minutes. The lysate is stored at 4° C. Stability of the lysate is inspected after 1, 4 and 7 days by visual inspection. The lysate stays optically clear over 7 days.

3.2 Potassiumthiocyanate with 1-Methyl-1-octylpyrrolidiniumchloride

This lysis reagent is prepared by mixing 23.7 mL potassiumthiocyanate solution (0.2 molar; 9.72 gram KSCN dissolved in 0.5 liter distilled water) with 1000 mg 1-methyl-1-octylpyrrolidiniumchloride (Me-octPCl) and 23.7 mL sodium chloride (0.15 molar in water). This reagent for differential hemolysis thus has a concentration of about 2% Me-octPCl.

250 microliter of EDTA-anticoagulated whole blood is pipetted into a vial containing 5 milliliter of this lysis reagent. For hemolysis the content of the tube is gently mixed by shaking. An optically clear lysate is obtained within five minutes. The lysate is stored at 4° C. Stability of the lysate is inspected after 1, 4 and 7 days by visual inspection. The lysate stays optically clear over 7 days.

3.3 1-Methyl-1-octylpyrrolidiniumchloride with potassiumthiocyanate

This as compared to Example 3.2 more concentrated lysis reagent is prepared by mixing 470 μL potassiumthiocyanate solution (1 molar) with 300 μL sodium chloride solution (0.15 molar in water) and 110 mg 1-methyl-1-octylpyrrolidiniumchloride. This reagent for differential hemolysis has a concentration of about 15% Me-octPCl.

20 microliter of EDTA-anticoagulated whole blood is pipetted into a container containing 80 microliter of this lysis reagent. For hemolysis the content of the tube is gently mixed by shaking. An optically clear lysate is obtained within five minutes. The lysate is stored at 4° C. Stability of the lysate is inspected after 1, and 2 days by visual inspection. The lysate stays optically clear.

3.4 3-Carbamoyl-1-octyloxymethylpyridiniumchloride

This lysis reagent is prepared by mixing 80 microliter water with 50 μL sodium chloride solution (0.15 molar in water) and 20 mg 3-Carbamoyl-1-octyloxymethylpyridiniumchloride. This reagent for differential hemolysis has a concentration of about 10% COMPCl.

50 microliter of EDTA-anticoagulated whole blood is pipetted into a container containing 130 microliter of this lysis reagent. For hemolysis the content of the tube is gently mixed by shaking. An optically clear lysate is obtained within five minutes. The lysate is stored at 4° C. Stability of the lysate is inspected after 1, and 2 days by visual inspection. The lysate stays optically clear.

From the above discussed experiments it is obvious to the skilled artisan that now it is possible and advantageous to include the anti-coagulant directly in the ready-to-use sampling tube thus resulting in a sampling tube containing a reagent for differential hemolysis of a whole blood sample, wherein said reagent for differential hemolysis also comprises an anti-coagulant.

What is claimed is:
1. A sampling tube for collecting and processing a whole blood sample, the sampling tube containing a reagent for differential hemolysis of said whole blood sample, wherein said reagent for differential hemolysis comprises a salt and an anti-coagulant, wherein said salt is selected from the group consisting of KBr, KJ, KSCN, and a salt consisting of a cation selected from the group consisting of

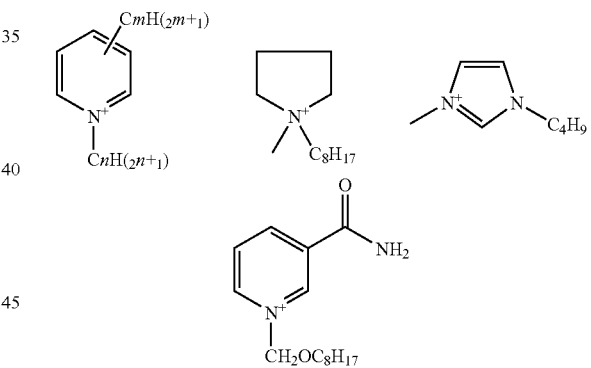

wherein m is 0 or 1 and n is 4 or 6, and an anion selected from the group consisting of chloride, tetrafluoroborate, octylsulfate, iodide and thiocyanate, wherein said sampling tube is a ready-to-use and single-use sampling tube, and wherein said differential hemolysis reagent if mixed 1:1 with a blood sample diluted 1:10 in physiological saline leads to a hemolysate of which 50 aliquots of 10 μL can be applied to a filter in an HPLC-system having a diameter of 2 mm and 0.5 μm pore size without blocking said filter.

2. The sampling tube according to claim 1, wherein said reagent for differential hemolysis causes the lysis of cell membranes of red blood cells and at the same time does not cause precipitation of sample constituents.

3. The sampling tube according to claim 1, wherein said reagent for differential hemolysis additionally comprises a protease inhibitor.

* * * * *